US00PP27054P3

(12) United States Plant Patent
Klemm et al.

(10) Patent No.: US PP27,054 P3
(45) Date of Patent: Aug. 9, 2016

(54) ***CALIBRACHOA* PLANT NAMED 'KLECA13244'**

(50) Latin Name: ***Calibrachoa* sp.**
Varietal Denomination: KLECA13244

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 172 days.

(21) Appl. No.: 14/121,075

(22) Filed: Jul. 28, 2014

(65) Prior Publication Data

US 2016/0029537 P1 Jan. 28, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new *Calibrachoa* plant particularly distinguished by having large orange-white flowers with red centers, a semi-trailing plant form and habit, and medium branching, is disclosed.

1 Drawing Sheet

Genus and species: *Calibrachoa* sp.
Variety denomination: 'KLECA13244'.

BACKGROUND OF THE NEW PLANT

The present invention comprises a new and distinct variety of *Calibrachoa*, botanically known as *Calibrachoa* sp., and hereinafter referred to by the variety name 'KLECA13244'. 'KLECA13244' originated from a controlled cross between the proprietary female *Calibrachoa* variety 'CA-2008-0791' (unpatented) and the proprietary male *Calibrachoa* variety 'CA-2009-1319' (unpatented) in May 2009 in Stuttgart, Germany.

In May 2009, seed was collected from the controlled cross between the two *Calibrachoa* parental lines. The seeds were sown and plants were grown for evaluation in Stuttgart, Germany. A single plant line was selected in May 2010 which had orange-white flowers with red centers and was subsequently named 'KLECA13244'. In May 2010, 'KLECA13244' was first vegetatively propagated by tip cuttings in Stuttgart, Germany. 'KLECA13244' was found to reproduce true to type in successive generations of asexual propagation via tip cuttings.

CROSS REFERENCE TO RELATED APPLICATION

Plant Breeder's Rights for 'KLECA13244' were applied for in Europe on Jun. 3, 2014, application number 2014/1521. 'KLECA13244' has not been made publicly available or sold more than one year prior to the filing date of this application.

SUMMARY

The following are the most outstanding and distinguishing characteristics of this new variety when grown under normal horticultural practices in Stuttgart, Germany.

1. Large, orange-white flowers with red centers;
2. A semi-trailing form and plant habit; and
3. Medium branching.

DESCRIPTION OF THE PHOTOGRAPH

This new *Calibrachoa* plant is illustrated by the accompanying photograph which shows the whole plant, including the habit, the foliage, the flowers, and the buds, and a close-up of the flowers. The photograph is of a seven-month-old plant grown in a pot in Stuttgart, Germany in June 2012. The colors shown are as true as can be reasonably obtained by conventional photographic procedures.

DESCRIPTION OF THE NEW VARIETY

The following detailed descriptions set forth the distinctive characteristics of 'KLECA13244'. The data which define these characteristics were collected from asexual reproductions carried out in Stuttgart, Germany. Data was collected on 11-week-old plants grown in a controlled glass greenhouse environment in Stuttgart, Germany in June 2014. Color references are to The R.H.S. Colour Chart of The Royal Horticultural Society of London (R.H.S.) (2007).

Classification:
- *Family*.—Solanaceae.
- *Botanical*.—*Calibrachoa* sp.
- *Common*.—*Calibrachoa*.
- *Designation*.—'KLECA13244'.

Parentage:
- *Female parent*.—Proprietary *Calibrachoa* line 'CA-2008-0791' (unpatented).
- *Male parent*.—Proprietary *Calibrachoa* line 'CA-2009-1319' (unpatented).

Plant:
- *Life cycle*.—Annual.
- *Form and habit*.—Semi-trailing.
- *Height (from soil line to top of foliage)*.—4.0 cm.

*Spread.*—28.0 cm.
*Propagation.*—Vegetatively propagated by tip cuttings.
*Time to produce a rooted cutting.*—18 days.
*Time to initiate roots.*—5 days at 20° C.
*Length of shoot cutting.*—5.0 cm.

Stems:
*Stem color.*—RHS 145B.
*Pubescence.*—Present.
*Pubescence color.*—RHS 145C.
*Diameter.*—0.2 cm.
*Length, from soil line to first node.*—1.2 cm.
*Total length.*—15.2 cm.
*Internode length.*—2.8 cm.

Leaves:
*Arrangement.*—Alternate, simple, and sessile.
*Shape.*—Broad elliptic.
*Apex.*—Obtuse to slightly acute.
*Base.*—Attenuate.
*Margin.*—Entire.
*Surface (both upper and lower surfaces).*—Smooth.
*Surface pubescence (both upper and lower surfaces).*—Absent.
*Variegation.*—Absent.
*Venation.*—Pinnate.
*Venation color.*—Upper surface: RHS 145A. Lower surface: RHS 145C.
*Length.*—4.2 cm.
*Width.*—1.5 cm.
*Color.*—Upper surface: RHS N147A. Lower surface: RHS 148B.
*Fragrance.*—Absent.
*Pedicel.*—Length: 2.7 cm. Diameter: 1.0 mm.

Flowers:
*Flowering habit.*—Flower attitude erect, single, and axillary.
*Flower type.*—Single flowers having determinate inflorescence.
*Flowering requirements.*—A minimum of light sun is required.
*Duration of flowers.*—5 days.
*Corolla texture.*—Medium texture.
*Corolla shape.*—Trumpet-shaped.
*Fragrance.*—Absent.
*Degree of lobing.*—Weak.

Flower buds:
*Surface texture.*—Smooth.
*Length.*—2.5 cm.
*Diameter.*—0.5 cm.
*Shape.*—Irregular to oblong.
*Color.*—RHS N162C and RHS N186D.

Peduncle:
*Length.*—2.7 cm.
*Diameter.*—0.1 cm.
*Color.*—RHS 147C.
*Texture.*—Smooth.
*Anthocyanin color.*—RHS 166A.

Flower description:
*Flower depth.*—3.0 cm.
*Flower tube length.*—2.0 cm.
*Flower tube diameter.*—0.8 cm.
*Flower diameter.*—4.5 cm.
*Pedicel color.*—RHS 147C.
*Calyx.*—Funnel-shaped.

Sepals:
*Shape.*—Lanceolate.
*Apex.*—Acute.
*Base.*—Fused.
*Margin.*—Entire.
*Length.*—1.7 cm.
*Diameter.*—0.4 cm.
*Texture (both upper and lower surfaces).*—Smooth.
*Sepal color.*—Upper surface: RHS 137A. Lower surface: RHS 137D.

Petals:
*Shape.*—Heart-shaped.
*Length.*—1.7 cm.
*Apex.*—Obverse.
*Margin.*—Entire, weak undulation.
*Base.*—Open and fused into the tube.
*Pubescence.*—Absent.
*Texture (both upper and lower surfaces).*—Smooth.
*Lobe length.*—1.7 cm.
*Lobe width.*—1.8 cm.
*Lobe color.*—Upper surface: RHS 159B. Lower surface: RHS 159C.
*Corolla tube color.*—Inner: RHS 46A. Outer: RHS 181C.
*Conspicuousness of the veins on the upper surface of the corolla lobe.*—Strong.
*Fragrance.*—Absent.

Reproductive organs:
*Stamen number.*—5.
*Stamen color.*—Anther color: RHS 7A. Anther shape: Ellipsoidal. Anther length: 0.7 mm. Filament color: RHS 10B. Filament length: 8.0 mm. Pollen color: RHS 7A. Pollen amount: Scarce.
*Ovary.*—Placenta arrangement: Ovate. Ovary color: RHS N144C. Pistil number: 1. Pistil length: 0.1 cm. Stigma color: RHS 154A. Style length: 0.8 cm. Style color: RHS 149B.

Fruit and seed set: Little seed production; description of seed not available.

Disease and pest/insect resistance: None observed.

COMPARISON WITH PARENTAL LINES AND KNOWN VARIETY

'KLECA13244' is distinguished from the female and male parental lines as described in Table 1.

TABLE 1

Comparison with Parental Lines

| Trait | 'KLECA13244' | Female parent 'CA-2008-0791' | Male Parent 'CA-2009-1319' |
|---|---|---|---|
| Flower color | RHS 159B and RHS 46A | Yellow with red veins | Pink with dark-pink eyes |

'KLECA13244' is most similar to the *Calibrachoa* plant named 'KLECA10211' (U.S. Plant Pat. No. 23,409). Differences between the two varieties are described in Table 2.

TABLE 2

| Comparison with Similar Variety | | |
|---|---|---|
| Trait | 'KLECA13244' | 'KLECA10211' |
| Flower size | Big | Medium |
| Branching | Medium | Poor |

We claim:

1. A new and distinct variety of *Calibrachoa* plant named 'KLECA13244' as illustrated and described herein.

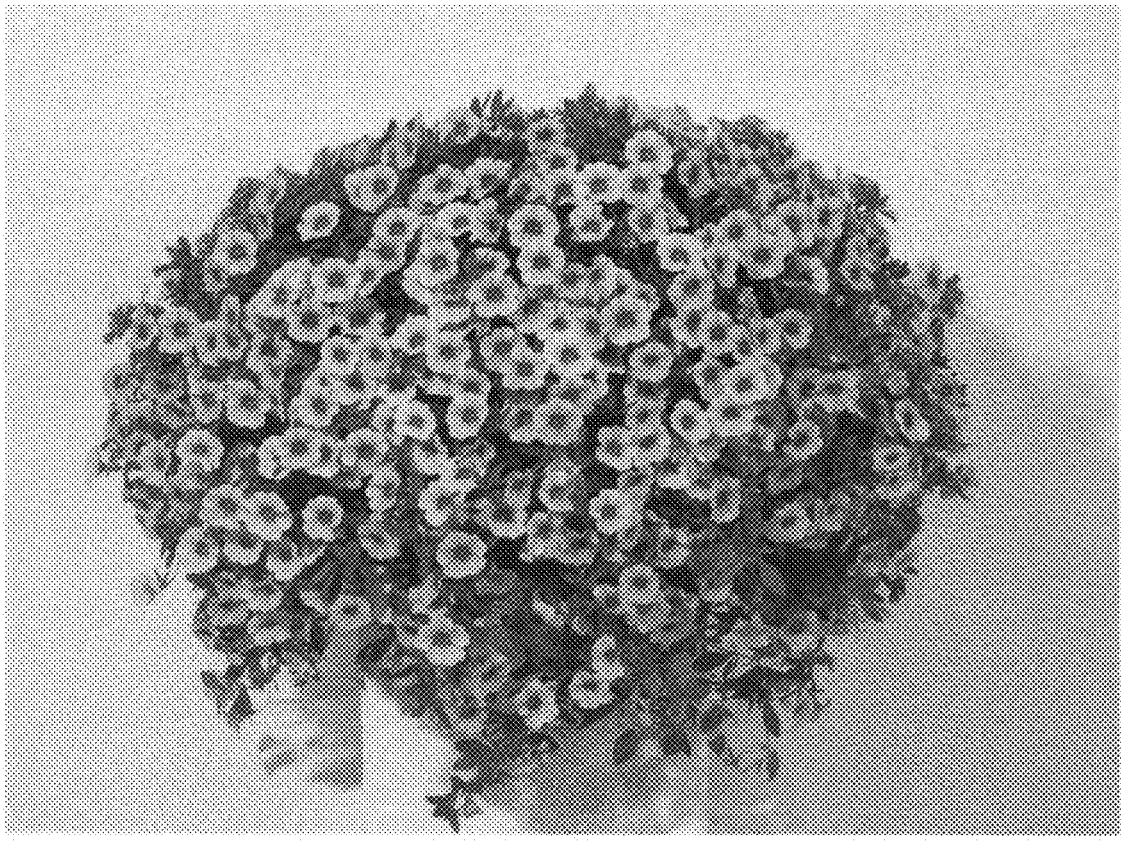

* * * * *